(12) United States Patent
Huang et al.

(10) Patent No.: US 11,903,531 B2
(45) Date of Patent: Feb. 20, 2024

(54) CLEANSING WIPE FORMED FROM A NONWOVEN INCLUDING ETHYLENE/ALPHA-OLEFIN INTERPOLYMERS

(71) Applicant: Dow Global Technologies LLC, Midland, MI (US)

(72) Inventors: Xin Huang, Shanghai (CN); Shijie Ren, Shanghai (CN); Yijian Lin, Pearland, TX (US); Jozef J. I. Van Dun, Antwerp (BE)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 17/756,533

(22) PCT Filed: Dec. 20, 2019

(86) PCT No.: PCT/CN2019/126868
§ 371 (c)(1),
(2) Date: May 26, 2022

(87) PCT Pub. No.: WO2021/120146
PCT Pub. Date: Jun. 24, 2021

(65) Prior Publication Data
US 2022/0408985 A1    Dec. 29, 2022

(51) Int. Cl.
*A47K 10/16* (2006.01)
*B32B 5/02* (2006.01)
(Continued)

(52) U.S. Cl.
CPC .............. *A47K 10/16* (2013.01); *B32B 5/022* (2013.01); *B32B 5/269* (2021.05); *D04H 1/4291* (2013.01); *D04H 1/43828* (2020.05); *D04H 1/724* (2013.01); *D04H 1/732* (2013.01); *B32B 2250/20* (2013.01); *B32B 2262/0253* (2013.01);
(Continued)

(58) Field of Classification Search
CPC ........ A47K 10/16; B32B 5/022; B32B 5/269; B32B 2262/124; B32B 2307/72; B32B 2262/0253; B32B 2555/00; B32B 2250/20; D04H 1/427; D04H 1/732; D04H 1/4291; D04H 1/43828; D10B 2509/00

See application file for complete search history.

(56) References Cited

U.S. PATENT DOCUMENTS 6,028,018 A    2/2000   Amundson et al.
7,064,091 B2   6/2006   Goldstein et al.
(Continued)

OTHER PUBLICATIONS

PCT/CN2019/126868, International Search Report and Written Opinion dated Sep. 24, 2020.

*Primary Examiner* — Jeremy R Pierce
(74) *Attorney, Agent, or Firm* — Boyle Fredrickson, S.C.

(57) ABSTRACT

A cleansing wipe may be formed from a nonwoven and includes a first ethylene/alpha-olefin interpolymer and a second ethylene/alpha-olefin interpolymer. The cleansing wipe may also have a SaMbSc configuration, wherein the M, meltblown layer, is formed from the first ethylene/alpha-olefin interpolymer and the second ethylene/alpha-olefin interpolymer. The cleansing wipe may be formed a nonwoven comprising bicomponent fibers that incorporate the first ethylene/alpha-olefin interpolymer and the second ethylene/alpha-olefin interpolymer.

10 Claims, 2 Drawing Sheets

(51) Int. Cl.
  *B32B 5/26*    (2006.01)
  *D04H 1/724*   (2012.01)
  *D04H 1/732*   (2012.01)
  *D04H 1/4291*  (2012.01)
  *D04H 1/4382*  (2012.01)

(52) U.S. Cl.
  CPC ..... *B32B 2262/124* (2021.05); *B32B 2307/72* (2013.01); *B32B 2555/00* (2013.01); *D10B 2509/00* (2013.01)

(56) References Cited

U.S. PATENT DOCUMENTS

| | | |
|---|---|---|
| 7,470,656 B2 | 12/2008 | Sherry et al. |
| 8,389,634 B2 | 3/2013 | Yalvac et al. |
| 9,803,295 B2 | 10/2017 | Patel et al. |
| 11,261,544 B2 * | 3/2022 | Shah .................... D04H 1/4291 |
| 2002/0174500 A1 | 11/2002 | Micciche et al. |
| 2003/0200991 A1 | 10/2003 | Keck et al. |
| 2005/0148261 A1 | 7/2005 | Close et al. |
| 2006/0166849 A1 | 7/2006 | Kilkenny et al. |
| 2010/0113706 A1 * | 5/2010 | Crowther ............. C08F 210/16 526/170 |
| 2011/0003524 A1 | 1/2011 | Claasen et al. |
| 2012/0171919 A1 | 7/2012 | Jackson et al. |
| 2013/0047365 A1 | 2/2013 | Goldwasser |
| 2013/0071630 A1 | 3/2013 | Weisman |
| 2013/0239344 A1 | 9/2013 | Stolarz, Jr. et al. |
| 2015/0086659 A1 | 3/2015 | Klofta et al. |
| 2015/0308039 A1 | 10/2015 | Bonaboglia et al. |
| 2017/0196414 A1 | 7/2017 | Erlandsson et al. |
| 2019/0211509 A1 | 7/2019 | Brennan et al. |
| 2020/0002849 A1 | 1/2020 | Shah et al. |

\* cited by examiner

FIGURE 1

FIGURE 2

CLEANSING WIPE FORMED FROM A NONWOVEN INCLUDING ETHYLENE/ALPHA-OLEFIN INTERPOLYMERS

TECHNICAL FIELD

The present invention generally relates to a cleansing wipe. More particularly, the invention relates to a cleansing wipe formed from a nonwoven that includes ethylene/alpha-olefin interpolymers.

Introduction

Nonwoven webs or fabrics are cloth-like materials that are manufactured from filaments which are brought together via different processes (e.g., spunbond or meltblown processes). Nonwovens are desirable for use in a variety of products such as bandaging materials and cleansing wipes, and nonwovens having improved levels of strength, softness, odor removal, moisture content retention, and liquid absorbency are desirable for disposable absorbent materials such as cleansing wipes.

Cleansing wipes may be formed via a spunlace process, where polymer fibers and cellulose fibers are mixed, formed into nonwoven fabrics, and bonded through spunlace or hydroentanglement processes. The spunlace process includes multiple steps, including manufacturing of staple fibers and manufacturing of nonwovens, which adds to the costs of the process used to form nonwovens.

Cleansing wipes may also be formed via a spunbond process. The spunbond process was historically used to form polypropylene monocomponent fibers due to its mechanical performance. Nonwoven fabrics made from polypropylene such as homo-polypropylene (hPP) via a spunbond process exhibit high modulus but poor elasticity and softness. These fabrics are often incorporated into multicomponent articles, including, for example, diapers, wound dressings, and feminine hygiene products. Softness can be improved by the introduction of polyethylene. For instance, spunbond layers may include bicomponent fibers having a polyethylene resin in the sheath and a polypropylene resin in the core. The polyethylene in the sheath provides softness and improved haptics, and the polypropylene in the core provides strength and fiber spinnability.

Cleansing wipes may also be formed via a meltblown process. A meltblown process used to form nonwovens such as cleansing wipes, results in thinner fibers, which improves softness. Polypropylene resins may be used to form the meltblown nonwovens because of its excellent processing characteristics in meltblown processes. However, forming nonwovens via a meltblown process presents problems with softness, moisture content retention, and liquid absorbency.

Because of the advantages and disadvantages associated with the different processes, fibers, and polymers used to form nonwovens, cleansing wipes including more than one layer are often formed in order to achieve a better balance of properties. Layers of the cleansing wipes may be identified by letters such as SMS for a three-layer cleansing wipe that includes an inner meltblown (M) layer and outer spunbond (S) layers. The layers of the cleansing wipe may be bonded together to maintain the structural integrity of the cleansing wipe. Common methods of bonding include point bonding, adhesive lamination, and other methods known to those skilled in the art.

Accordingly, there is a need in the art for less costly and more efficiently produced cleansing wipes with improved softness, haptics, moisture content retention, and liquid absorbency. The invention disclosed herein provides a solution to this need.

SUMMARY

Disclosed herein are cleansing wipes formed from a nonwoven that include ethylene/alpha-olefin interpolymers. The cleansing wipe formed from a nonwoven comprises a first ethylene/alpha-olefin interpolymer having a density of from 0.911 to 0.939 g/cc, a Brookfield viscosity of less than or equal to 50,000 cP, and a molecular weight distribution ($M_{w,CC}/M_{n,CC}$) of 1.8 to 3.5; and from 2.5 wt. % to 25 wt. % of a second ethylene/alpha-olefin interpolymer having a density of less than 0.900 g/cc and a melt index (I2) of at least 10 g/10 min.

Also disclosed herein are cleansing wipes having a $S_aM_bS_c$ configuration. The cleansing wipe has a $S_aM_bS_c$ configuration, wherein S is a spunbond nonwoven and M is a meltblown layer, "a" and "c" are the number of layers of S and are independent integers ranging from 0 to 5, and "b" is the number of layers of M and is an independent integer ranging from 1 to 5; and wherein M comprises a first ethylene/alpha-olefin interpolymer having a density of from 0.911 to 0.939 g/cc, a Brookfield viscosity of less than or equal to 50,000 cP, and a molecular weight distribution ($M_{w,CC}/M_{n,CC}$) of 1.8 to 3.5, and from 2.5 wt. % to 25 wt. % of a second ethylene/alpha-olefin interpolymer having a density of less than 0.900 g/cc and a melt index (I2) of at least 10 g/10 min.

Also disclosed herein are cleansing wipes including bicomponent fibers. The cleansing wipe formed from a nonwoven comprises a bicomponent fiber, wherein: the bicomponent fiber has a first region and a second region, the first region is formed from a first composition comprising at least 75 wt. % of a polypropylene; the second region is formed from a second composition comprising a first ethylene/alpha-olefin interpolymer having a density of from 0.911 to 0.939 g/cc, a Brookfield viscosity of less than or equal to 50,000 cP, and a molecular weight distribution ($M_{w,CC}/M_{n,CC}$) of 1.8 to 3.5, and from 2.5 wt. % to 25 wt. % of a second ethylene/alpha-olefin interpolymer having a density of less than 0.900 g/cc and a melt index (I2) of at least 10 g/10 min.

In one or more embodiments, the second ethylene/alpha-olefin interpolymer has a density from 0.850 to 0.890 g/cc and a melt index (I2) of from 10 g/10 min to 600 g/10 min. In one or more embodiments, the second ethylene/alpha-olefin interpolymer is an ethylene/alpha-olefin block copolymer. In one or more embodiments, the first ethylene/alpha-olefin interpolymer has an $M_{z,cc}/M_{n,cc}$ less than 4.0, or alternatively, less than 3.5. In one or more embodiments, the first ethylene/alpha-olefin interpolymer has a weight fraction (w) of molecular weight greater than $10^5$ g/mole, based on the total weight of the first ethylene/alpha-olefin interpolymer, as determined by conventional gel permeation chromatography, of less than 2.5%, or alternatively, less than 1.0%. In one or more embodiments, the first ethylene/alpha-olefin interpolymer has a comonomer distribution breadth index of greater than 50%, or alternatively, from 50% to 98%, or alternatively, 50% to 85%. In one or more embodiments, the moisture content (%) of the cleansing wipe after hanging for 20 minutes is greater than 800%. In one or more embodiments, the cleansing wipe further comprises one or more spunbond nonwovens.

Additional features and advantages of the embodiments will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing and the following description describe various embodiments and are intended to provide an overview or framework for understanding the nature and character of the claimed subject matter.

DETAILED DESCRIPTION

Aspects of the disclosed cleansing wipes are described in more detail below. It is noted, however, that the below is merely an illustrative implementation of the aspects of the invention. The embodiments of the present invention are applicable to other technologies that are susceptible to similar problems as those discussed above.

As used herein, the term "cleansing wipe" refers to a sheet for cleaning or removing material, including, without limitation, solid or liquid material, from a surface (e.g., skin). The cleansing wipe may be impregnated with a liquid solution. The term "cleansing wipe" includes, for example, hand wipes, face wipes, cosmetic wipes, cosmetic facial masks, household wipes, and industrial wipes.

As used herein, the terms "nonwoven," "nonwoven web," and "nonwoven fabric" are used herein interchangeably. "Nonwoven" refers to a web or fabric having a structure of individual fibers or threads which are randomly interlaid, but not in an identifiable manner as is the case for a knitted fabric.

As used herein, the term "interpolymer" refers to a polymer prepared by the polymerization of at least two different types of monomers. The term "interpolymer" includes the term "copolymer" (which is usually employed to refer to a polymer prepared from two different monomers) as well as the term "terpolymer" (which is usually employed to refer to a polymer prepared from three different types of monomers). It also encompasses polymers made by polymerizing four or more types of monomers.

Ethylene/Alpha-Olefin Interpolymers of the Cleansing Wipe

The term "ethylene/alpha-olefin interpolymer" generally refers to polymers comprising ethylene and an alpha-olefin having 3 or more carbon atoms. In embodiments herein, the cleansing wipe formed from a nonwoven includes a first ethylene/alpha-olefin interpolymer and a second ethylene/alpha-olefin interpolymer. Each of the ethylene/alpha-olefin interpolymers comprises greater than 70 wt. % of the units derived from ethylene and less than 30 wt. % of the units derived from one or more alpha-olefin comonomers (based on the total amount of polymerizable monomers). All individual values and subranges of greater than 70 wt. % of the units derived from ethylene and less than 30 wt. % of the units derived from one or more alpha-olefin comonomers are included and disclosed herein. For example, in one or more embodiments, either or both of the ethylene/alpha-olefin interpolymers may comprise (a) greater than or equal to 75%, greater than or equal to 80%, greater than or equal to 85%, greater than or equal to 90%, greater than or equal to 92%, greater than or equal to 95%, greater than or equal to 97%, greater than or equal to 98%, greater than or equal to 99%, greater than or equal to 99.5%, from greater than 70% to 99%, from greater than 70% to 97%, from greater than 70% to 94%, from greater than 70% to 90%, from 70% to 99.5%, from 70% to 99%, from 70% to 97% from 70% to 94%, from 80% to 99.5%, from 80% to 99%, from 80% to 97%, from 80% to 94%, from 80% to 90%, from 85% to 99.5%, from 85% to 99%, from 85% to 97%, from 88% to 99.9%, 88% to 99.7%, from 88% to 99.5%, from 88% to 99%, from 88% to 98%, from 88% to 97%, from 88% to 95%, from 88% to 94%, from 90% to 99.9%, from 90% to 99.5% from 90% to 99%, from 90% to 97%, from 90% to 95%, from 93% to 99.9%, from 93% to 99.5% from 93% to 99%, or from 93% to 97%, by weight, of the units derived from ethylene; and (b) less than 30 percent, for example, less than 25 percent, or less than 20 percent, less than 18%, less than 15%, less than 12%, less than 10%, less than 8%, less than 5%, less than 4%, less than 3%, less than 2%, less than 1%, from 0.1 to 20%, from 0.1 to 15%, 0.1 to 12%, 0.1 to 10%, 0.1 to 8%, 0.1 to 5%, 0.1 to 3%, 0.1 to 2%, 0.5 to 12%, 0.5 to 10%, 0.5 to 8%, 0.5 to 5%, 0.5 to 3%, 0.5 to 2.5%, 1 to 10%, 1 to 8%, 1 to 5%, 1 to 3%, 2 to 10%, 2 to 8%, 2 to 5%, 3.5 to 12%, 3.5 to 10%, 3.5 to 8%, 3.5% to 7%, or 4 to 12%, 4 to 10%, 4 to 8%, or 4 to 7%, by weight, of units derived from one or more α-olefin comonomers. The comonomer content may be measured using any suitable technique, such as techniques based on nuclear magnetic resonance ("NMR") spectroscopy, and, for example, by $^{13}C$ NMR analysis as described in U.S. Pat. No. 7,498,282, which is incorporated herein by reference.

Suitable alpha-olefin comonomers typically have no more than 20 carbon atoms. The one or more alpha-olefins may be selected from the group consisting of C3-C20 acetylenically unsaturated monomers and C4-C18 diolefins. For example, the alpha-olefin comonomers may have 3 to 10 carbon atoms, or 3 to 8 carbon atoms. Exemplary alpha-olefin comonomers include, but are not limited to, propylene, 1-butene, 1-pentene, 1-hexene, 1-heptene, 1-octene, 1-nonene, 1-decene, and 4-methyl-1-pentene. The one or more alpha-olefin comonomers may, for example, be selected from the group consisting of propylene, 1-butene, 1-hexene, and 1-octene; or in the alternative, from the group consisting of 1-butene, 1-hexene and 1-octene, or in the alternative, from the group consisting of 1-hexene and 1-octene. In one or more embodiments, each of the ethylene/alpha-olefin interpolymers may comprise greater than 0 wt. % and less than 30 wt. % of units derived from one or more of 1-octene, 1-hexene, or 1-butene comonomers.

In embodiments described herein, the cleansing wipe comprises a first ethylene/alpha-olefin interpolymer having a density of 0.911 to 0.939 grams/cubic centimeter (g/cc). All individual values and subranges of from 0.911 to 0.939 g/cc are included and disclosed herein. For example, in one or more embodiments, the first ethylene/alpha-olefin interpolymer has a density of 0.911 to 0.935 g/cc. In other embodiments, the first ethylene/alpha-olefin interpolymer has a density of 0.913 to 0.939 g/cc. In further embodiments, the first ethylene/alpha-olefin interpolymer has a density of 0.913 to 0.935 g/cc. Density may be measured according to ASTM D792.

In addition to the density, the first ethylene/alpha-olefin interpolymer has a Brookfield viscosity of less than or equal to 50,000 centipoise (cP). All individual values and subranges of less than or equal to 50,000 cP are included and disclosed herein. For example, in one or more embodiments, the first ethylene/alpha-olefin interpolymer has a Brookfield viscosity of less than or equal to 45,000 cP, less than or equal to 40,000 cP, or less than or equal to 35,000 cP. In other embodiments, the first ethylene/alpha-olefin interpolymer has a Brookfield viscosity of from 5,000 cP to 50,000 cP, from 5,000 cP to 45,000 cP, or 5,000 cP to 40,000 cP.

In addition to the density and Brookfield viscosity, the first ethylene/alpha-olefin interpolymer has a molecular weight distribution ($M_{w,cc}/M_{n,cc}$) of from 1.8 to 3.5. Molecular weight distribution can be described as the ratio of weight-average molecular weight ($M_{w,cc}$) to number-average molecular weight ($M_{n,cc}$) (i.e., $M_{w,cc}/M_{n,cc}$), and can be measured by gel permeation chromatography (GPC) techniques. All individual values and subranges of from 1.8 to 3.5 are included and disclosed herein. For example, in one or more embodiments, the first ethylene/alpha-olefin interpolymer has a molecular weight distribution ($M_{w,cc}/M_{n,cc}$) of from 1.9 to 3.5 or 2.0 to 3.5. In other embodiments, the first ethylene/alpha-olefin interpolymer has a molecular weight distribution ($M_{w,cc}/M_{n,cc}$) of from 1.8 to 3.0, 1.9 to 3.0, or 2.0 to 3.0. In further embodiments, the first ethylene/alpha-olefin interpolymer has a molecular weight distribution ($M_{w,cc}/M_{n,cc}$) of from 1.8 to 2.8, 1.9 to 2.8, or 2.0 to 2.8.

In addition to the density, Brookfield viscosity, and molecular weight distribution, the first ethylene/alpha-olefin interpolymer may have an $M_{z,cc}/M_{n,cc}$ of less than 4.0. $M_{z,cc}$ can be described as the z average molecular weight. All individual values and subranges of less than 4.0 are included and disclosed herein. For example, in one or more embodiments, the first ethylene/alpha-olefin interpolymer has a $M_{z,cc}/M_{n,cc}$ of less than 3.5. In other embodiments, the first ethylene/alpha-olefin interpolymer has a $M_{z,cc}/M_{n,cc}$ of from 2.5 to 4.0 or from 2.5 to 3.5.

In addition to the density, Brookfield viscosity, molecular weight distribution, and $M_{z,cc}/M_{n,cc}$, the first ethylene/alpha-olefin interpolymer may have a weight fraction (w) of molecular weight greater than $10^5$ g/mole, based on the total weight of the first ethylene/alpha-olefin interpolymer, as determined by conventional gel permeation chromatography, of less than 2.5%. All individual values and subranges of less than 2.5% are included and disclosed herein. For example, in one or more embodiments, the first ethylene/alpha-olefin interpolymer has a weight fraction (w) of molecular weight greater than $10^5$ g/mole, based on the total weight of the first ethylene/alpha-olefin interpolymer, as determined by conventional gel permeation chromatography, of less than 1.0%.

In addition to the density, Brookfield viscosity, molecular weight distribution, $M_{z,cc}/M_{n,cc}$, and weight fraction (w) of molecular weight greater than $10^5$ g/mole, the first ethylene/alpha-olefin interpolymer may have a comonomer distribution breadth index (CDBI) of greater than or equal to 50%. All individual values and subranges of greater than or equal to 50% are included and disclosed herein. For example, in one or more embodiments, the first ethylene/alpha-olefin interpolymer has a CDBI of greater than or equal to 55%, greater than or equal to 60%, greater than or equal to 65%, greater than or equal to 70%, or greater than or equal to 75%. In other embodiments, the first ethylene/alpha-olefin interpolymer has a CDBI ranging from 50% to 98%, 50% to 97%, 55% to 98%, 55% to 97%, 60% to 98%, 60% to 97%, 70% to 98%, 70% to 97%, 75% to 98%, or 75% to 97%. In further embodiments, the first ethylene/alpha-olefin interpolymer has a CDBI ranging from 50% to 85%, 55% to 85%, 60% to 85%, 60% to 80%, 65% to 80%, or 70% to 80%.

In addition to the density, Brookfield viscosity, molecular weight distribution, $M_{z,cc}/M_{n,cc}$, weight fraction (w) of molecular weight greater than $10^5$ g/mole, and CDBI, the first ethylene/alpha-olefin interpolymer may have a highest DSC temperature crystallization peak, Tc, of from 80° C. to 110° C. All individual values and subranges of from 80° C. to 110° C. are included and disclosed herein. For example, in one or more embodiments, the first ethylene/alpha-olefin interpolymer has a Tc of from 80° C. to 105° C., from 85° C. to 105° C., or from 90° C. to 105° C. In other embodiments, the first ethylene/alpha-olefin interpolymer has a Tc of from 95° C. to 105° C. The highest DSC temperature crystallization peak is determined using the differential scanning calorimetry (DSC) method outlined below.

In addition to the density, Brookfield viscosity, molecular weight distribution, $M_{z,cc}/M_{n,cc}$, weight fraction (w) of molecular weight greater than $10^5$ g/mole, CDBI, and Tc, the first ethylene/alpha-olefin interpolymer may have a temperature differential between the highest DSC temperature melting peak (Tm) and the highest DSC temperature crystallization peak (Tc), ΔTm−Tc, of less than 16° C. All individual values and subranges of less than 16° C. are included and disclosed herein. For example, in one or more embodiments, the first ethylene/alpha-olefin interpolymer may have a ΔTm−Tc of less than 15° C. In other embodiments, the first ethylene/alpha-olefin interpolymer may have a ΔTm−Tc of less than 12° C. The highest DSC temperature melting peak (Tm) is determined using the differential scanning calorimetry (DSC) method outlined below.

In embodiments described herein, the cleansing wipe comprises a second ethylene/alpha-olefin interpolymer having a density of less than 0.900 grams/cubic centimeter (g/cc). All individual values and subranges of a density less than 0.900 g/cc are included and disclosed herein. For example, in one or more embodiments, the second ethylene/alpha-olefin interpolymer has a density of less than 0.895 g/cc, less than 0.890 g/cc, less than 0.885 g/cc, or less than 0.880 g/cc. In other embodiments, the second ethylene/alpha-olefin interpolymer has a density of from 0.850 g/cc to 0.890 g/cc, 0.850 g/cc to 0.880 g/cc, 0.850 g/cc to 0.870 g/cc, 0.860 g/cc to 0.890 g/cc, 0.860 g/cc to 0.880 g/cc, 0.860 g/cc to 0.870 g/cc, 0.870 g/cc to 0.900 g/cc, from 0.875 g/cc to 0.900 g/cc, from 0.870 g/cc to 0.890 g/cc, or from 0.870 g/cc to 0.880 g/cc. Density may be measured according to ASTM D792. In addition to the density, the second ethylene/alpha-olefin interpolymer has a melt index (I2) of at least 10 g/10 min. All individual values and subranges of a melt index (I2) of at least 10 g/10 min are included and disclosed herein. For example, in one or more embodiments, the second ethylene/alpha-olefin interpolymer has a melt index (I2) of at least 15 g/10 min, at least 20 g/10 min, or at least 25 g/10 min. In other embodiments, the second ethylene/alpha-olefin interpolymer has a melt index (I2) of from 10 g/10 min to 20 g/10 min, from 10 g/10 min to 40 g/10 min, from 10 g/10 min to 400 g/10 min, from 10 g/10 min to 600 g/10 min, from 20 g/10 min to 40 g/10 min, from 20 g/10 min to 100 g/10 min, from 20 g/10 min to 1,000 g/10 min, from 20 g/10 min to 1,200 g/10 min, from 20 g/10 min to 1,500 g/10 min, from 200 g/10 min to 400 g/10 min, from 200 g/10 min to 600 g/10 min, from 200 g/10 min to 1,000 g/10 min, from 200 g/10 min to 1,200 g/10 min, from 200 g/10 min to 1,500 g/10 min, from 500 g/10 min to 600 g/10 min, from 500 g/10 min to 800 g/10 min, from 500 g/10 min to 1,000 g/10 min, from 500 g/10 min to 1,200 g/10 min, from 500 g/10 min to 1,500 g/10 min, from 800 g/10 min to 1,500 g/10 min, from 800 g/10 min to 1,200 g/10 min, from 800 g/10 min to 1,000 g/10 min, from 1,000 g/10 min to 1,500 g/10 min, or from 1,000 g/10 min to 1,200 g/10 min. Melt index (I2) may be determined according to ASTM D 1238 (190° C./2.16 kg).

In embodiments herein, the cleansing wipe formed from a nonwoven comprises from 75 wt. % to 97.5 wt. % of the first ethylene/alpha-olefin interpolymer. All individual values and subranges of from 75 wt. % to 97.5 wt. % are included and disclosed herein. For example, in one or more embodiments, the cleansing wipe formed from the nonwoven comprises from 75 wt. % to 95 wt. %, 75 wt. % to 90 wt. %, 75 wt. % to 85 wt. %, 75 wt. % to 80 wt. %, 80 wt. % to 95 wt. %, 80 wt. % to 90 wt. %, 80 wt. % to 85 wt. %, 85 wt. % to 95 wt. %, 85 wt. % to 90 wt. %, or 90 wt. % to 95 wt. % of the first ethylene/alpha-olefin interpolymer. In embodiments described herein, in addition to the first ethylene/alpha-olefin interpolymer, the cleansing wipe formed from the nonwoven comprises from 2.5 wt. % to 25 wt. % of the second ethylene/alpha-olefin interpolymer. All individual values and subranges of from 2.5 wt. % to 25 wt. % are included and disclosed herein. For example, in one or more embodiments, the cleansing wipe formed from the nonwoven comprises from 2.5 wt. % to 20 wt. %, 5 wt. % to 20 wt. %, 7.5 wt. % to 20 wt. %, 10 wt. % to 20 wt. %, 10 wt. % to 17.5 wt. %, 10 wt. % to 15 wt. %, or 10 wt. % to 12.5 wt. % of the second ethylene/alpha-olefin interpolymer.

In embodiments herein, the first ethylene/alpha-olefin interpolymer or the second ethylene/alpha-olefin interpolymer may be prepared in a solution polymerization process using one or more conventional reactors e.g. loop reactors, isothermal reactors, plug flow reactors, and/or stirred tank reactors in parallel, series, and/or any combinations thereof in continuous or batch mode to produce olefin based polymers, e.g. ethylene polymers or propylene polymers. The solution phase polymerization process may occur in one or more well-stirred reactors, such as one or more loop reactors or one or more isothermal reactors, at a temperature in the range of from 100 to 300° C.; for example, from 120 to 190° C., and at pressures in the range of from 300 to 1,000 psig; for example, from 400 to 750 psig. The residence time in solution phase polymerization process is typically in the range of from 2 to 30 minutes; for example, from 5 to 20 minutes. Ethylene (monomer), solvent, hydrogen, one or more catalyst systems, and one or more comonomers are fed continuously to the reactor. Exemplary solvents include, but are not limited to, isoparaffins and naphthinics. For example, such solvents are commercially available under the name ISOPAR E from ExxonMobil Chemical Co., Houston, Texas or under the name SBP 100/140 from Shell Chemicals Europe. The effluent from the polymerization reactor (containing solvent, monomer, comonomer, hydrogen, catalyst components, and molten polymer) exits the reactor and enters a zone where it is contacted with a deactivating agent and, optionally, an acid scavenging agent (such as calcium stearate and the accompanying water of hydration) to stop the reaction and scavenge hydrogen chloride. In addition, various additives, such as antioxidants, can be added at this point. The stream then goes through another set of static mixing elements, such as Kenics helical static mixing elements, to evenly disperse the catalyst kill and additives. The effluent (containing solvent, monomer, comonomer, hydrogen, catalyst components, and molten polymer) passes through a heat exchanger to raise the stream temperature in preparation for separation of the polymer from the other lower boiling reaction components. The stream then passes through a pressure let down control valve, which is responsible for maintaining the pressure of the reactor at a specified target. The stream then enters a multi-stage separation and devolatilization system where the polymer is removed from the solvent, hydrogen, and unreacted monomer and comonomer. Impurities are removed from the recycled, lower boiling reaction components before entering the reactor again. The separated and devolatilized polymer melt is pumped through a heat exchanger to lower the stream temperature to a temperature in the range of less than 200° C., for example less than 170° C., or in the range of from 50 to 110° C.; thereby producing a cooled polymer melt. Subsequently, the cooled polymer melt is pumped through a die specially designed for underwater pelletization, cut into uniform solid pellets, dried, and transferred into a hopper. After validation of initial polymer properties, the solid polymer pellets are transferred to storage devices. The portions removed in the devolatilization step may be recycled or destroyed. For example, most of the solvent is recycled back to the reactor after passing through purification beds. This recycled solvent can still have unreacted co-monomer in it that is fortified with fresh co-monomer prior to re-entry to the reactor. This recycle solvent can also have some hydrogen which is then fortified with fresh hydrogen.

In one or more embodiments, the first ethylene/alpha-olefin interpolymer or the second ethylene/alpha-olefin interpolymer may be prepared using a catalyst composition via a solution phase polymerization process in a loop reactor in accordance with the following procedure. All raw materials (ethylene, and one or more alpha-olefin comonomers, such as hexene or octene) and the process solvent (an isoparaffinic solvent, for example ISOPAR E) are purified with molecular sieves before introduction into the reaction environment. Hydrogen is supplied as a high purity grade and is not further purified. The reactor monomer feed (ethylene) stream is pressurized via a mechanical compressor to a pressure that is above the reaction pressure, e.g. 750 psig. The solvent and comonomer (one or more alpha-olefin comonomer, such as hexene or octene) feed is pressurized via a mechanical positive displacement pump to a pressure that is above the reaction pressure, e.g. 750 psig. The individual catalyst components can be manually batch diluted to specified component concentrations with purified solvent (ISOPAR E) and pressurized to a pressure that is above the reaction pressure, e.g. 750 psig. All reaction feed flows can be measured with mass flow meters and independently controlled with computer automated valve control systems.

The continuous solution polymerization reactor may consist of a liquid full, non-adiabatic, isothermal, circulating, loop. Independent control of all fresh solvent, monomer, comonomer, hydrogen, and catalyst component feeds is possible. The combined solvent, monomer, comonomer and hydrogen feed is temperature controlled to anywhere between 5° C. to 50° C. and typically 40° C. by passing the feed stream through a heat exchanger. The fresh comonomer feed to the polymerization reactor is aligned to add comonomer to the recycle solvent. The total fresh feed to the polymerization reactor is injected into the reactor at, for example, two locations roughly with equal reactor volumes between each injection location. The fresh feed is controlled typically with each injector, for example, receiving half of the total fresh feed mass flow. The catalyst components are injected into the polymerization reactor through, for example, a specially designed injection inlet device and are combined into one mixed procatalyst/cocatalyst feed stream prior to injection into the reactor. The procatalyst component feed is computer controlled to maintain the reactor monomer concentration at a specified target. The cocatalyst component is fed based on calculated specified molar ratios to the procatalyst component. Immediately following each fresh injection location (either feed or catalyst), the feed streams are mixed with the circulating polymerization reactor contents with static mixing elements, such as Kenics helical static mixing elements. The contents of the reactor are continuously circulated through heat exchangers responsible for removing much of the heat of reaction and with the temperature of the coolant side responsible for maintaining an isothermal reaction environment at the specified temperature. Circulation around the reactor loop can be provided by a screw pump. The effluent from the polymerization reactor (containing solvent, monomer, comonomer, hydrogen, catalyst components, and molten polymer) exits the reactor and enters a zone where it is contacted with a deactivating and, optionally, an acid scavenging agent (e.g., calcium stearate and the accompanying water of hydration) to stop the reaction and scavenge hydrogen chloride. In addition, various additives such as antioxidants can be added at this point. The stream then goes through another set of static mixing elements, such as Kenics helical static mixing elements to evenly disperse the catalyst kill and additives. The effluent (containing solvent, monomer, comonomer, hydrogen, catalyst components, and molten polymer) passes through a heat exchanger to raise the stream temperature in preparation for separation of the polymer from the other lower boiling reaction components. The stream then passes through a pressure let down control valve, which is responsible for maintaining the pressure of the reactor at a specified target. The stream then enters a two stage separation and devolatilization system where the polymer is removed from the solvent, hydrogen, and unreacted monomer and comonomer. Impurities are removed from the recycled low boiling reaction components before entering the reactor again. The separated and devolatilized polymer melt is pumped through a heat exchanger to lower the stream temperature to a temperature in the range of less than 200° C., for example less than 170° C., or in the range of from 50 to 110° C.; thereby producing a cooled polymer melt. Subsequently, the cooled polymer melt is pumped through a die specially designed for underwater pelletization, cut into uniform solid pellets, dried, and transferred into a hopper. After validation of initial polymer properties, the solid polymer pellets are transferred to storage devices. The portions removed in the devolatilization step may be recycled or destroyed. For example, most of the solvent is recycled back to the reactor after passing through purification beds. This recycled solvent can still have unreacted co-monomer in it that is fortified with fresh co-monomer prior to re-entry to the reactor. This recycle solvent can still have some hydrogen which is then fortified with fresh hydrogen.

In other embodiments, the first ethylene/alpha-olefin interpolymer or the second ethylene/alpha-olefin interpolymer may be prepared using one or more catalyst systems suitable for polymerizing ethylene and one or more alpha-olefin comonomers via a solution phase polymerization process in two adiabatic stirred-tank reactors, linked together in series in accordance to the following procedure. The ethylene monomer and one or more alpha-olefin comonomers, and hydrogen are combined with a solvent, e.g. an isoparaffinic solvent, such as ISOPAR E. Impurities such as water, carbon dioxide, sulfurous compounds are removed from the feed streams, and the feed streams are cooled to temperature in the range of 5° C. to 60° C., for example, approximately 13° C., before entering the reactor. The majority, approximately from 85 to 90 percent, of the reaction may occur in the first adiabatic stirred-tank reactor. The mixing may be achieved via circulating the polymer/procatalyst/cocatalyst/solvent/ethylene/one or more alpha-olefin comonomers/hydrogen solution with one or more agitators equipped with mixing blades. The feed (ethylene/one or more alpha-olefin comonomers/solvent/hydrogen) may, for example, enter the reactor from the bottom and the procatalyst/cocatalyst may, for example, enter the reactor separately from the feed and also from the bottom. The first reactor temperature is in the range of from 120° C. to 190° C., for example, approximately 175° C., and the reactor pressure is in the range of from 400 psig to 1,000 psig, for example, approximately 500 psig. The temperature of the second reactor, in series with the first reactor, increases to a temperature in the range of from 175° C. to 210° C., for example, approximately 202° C. with approximately from 10 to 15 percent of the remaining reaction occurring and no additional catalyst or monomers are added. The average reactor residence time is in the range of from 2 to 30 minutes, for example, approximately 8 minutes per adiabatic stirred-tank reactor prior to termination post-reactor by a fluid specially designed for that purpose.

The effluent from the polymerization reactor (containing solvent, monomer, comonomer, hydrogen, catalyst components, and molten polymer) exits the reactor and enters a zone where it is contacted with a deactivating and optionally an acid scavenging agent (e.g., calcium stearate and the accompanying water of hydration) to stop the reaction and scavenge hydrogen chloride. In addition, various additives such as antioxidants can be added at this point. The stream then goes through another set of static mixing elements, such as Kenics helical static mixing elements to evenly disperse the catalyst kill and additives. The effluent (containing solvent, monomer, comonomer, hydrogen, catalyst components, and molten polymer) passes through a heat exchanger to raise the stream temperature in preparation for separation of the polymer from the other lower boiling reaction components. The stream then passes through a pressure let down control valve, which is responsible for maintaining the pressure of the reactor at a specified target. The stream then enters a two stage separation and devolatilization system where the polymer is removed from the solvent, hydrogen, and unreacted monomer and comonomer. Impurities are removed from the recycled lower boiling reaction components before entering the reactor again. The separated and devolatilized polymer melt is pumped through a heat exchanger to lower the stream temperature to a temperature in the range of less than 200° C., for example less than 170° C., or in the range of from 50 to 110° C.; thereby producing a cooled polymer melt. Subsequently, the cooled polymer melt is pumped through a die specially designed for underwater pelletization, cut into uniform solid pellets, dried, and transferred into a hopper. After validation of initial polymer properties, the solid polymer pellets are transferred to storage devices. The portions removed in the devolatilization step may be recycled or destroyed. For example, most of the solvent is recycled back to the reactor after passing through purification beds. This recycled solvent can still have unreacted co-monomer in it that is fortified with fresh co-monomer prior to re-entry to the reactor. This recycle solvent can still have some hydrogen which is then fortified with fresh hydrogen.

Ethylene-α-Olefin Block Copolymer

In one or more embodiments herein, the second ethylene/alpha-olefin interpolymer of the cleansing wipe is an ethylene/alpha-olefin block copolymer.

The term "ethylene-α-olefin block copolymer" or "OBC" means an ethylene/α-olefin multi-block copolymer and includes ethylene and one or more copolymerizable α-olefin comonomer in polymerized form, and is characterized by multiple blocks or segments of two or more polymerized monomer units differing in chemical or physical properties. When referring to amounts of "ethylene" or "comonomer" in the copolymer, it is understood that this means polymerized units thereof. The ethylene-α-olefin block copolymer used in embodiments described herein can be represented by the following formula:

where: n is at least 1, and, in one or more embodiments, an integer greater than 1, such as 2, 3, 4, 5, 10, 15, 20, 30, 40, 50, 60, 70, 80, 90, 100, or higher; "A" represents a hard block or segment; and "B" represents a soft block or segment. In one or more embodiments, As and Bs are linked in a substantially linear fashion, as opposed to a substantially branched or substantially star-shaped fashion. In other embodiments, A blocks and B blocks are randomly distributed along the polymer chain. In other words, the block copolymer usually does not have a structure as follows.

In still other embodiments, the ethylene-α-olefin block copolymer described herein does not usually have a third type of block, which comprises a different comonomer(s). In yet other embodiments, each of block A and block B has monomers or comonomers substantially randomly distributed within the block. In other words, neither block A nor block B comprises two or more sub-segments (or sub-blocks) of distinct composition, such as a tip segment, which has a substantially different composition than the rest of the block.

In embodiments herein, ethylene may comprise the majority mole fraction of the whole ethylene-α-olefin block copolymer, i.e., ethylene comprises at least 50 mol. % of the whole polymer. In one or more embodiments, ethylene comprises at least 60 mol. %, at least 70 mol. %, or at least 80 mol. %. The substantial remainder of the whole polymer comprises at least one other comonomer that is an α-olefin having 3 or more carbon atoms. In one or more embodiments, the ethylene-α-olefin block copolymer described herein may comprise 50 mol. % to 90 mol. %, 60 mol. % to 85 mol. %, or 65 mol. % to 80 mol. % of ethylene. The comonomer content may be measured using any suitable technique, such as techniques based on nuclear magnetic resonance ("NMR") spectroscopy, and, for example, by $^{13}C$ NMR analysis as described in U.S. Pat. No. 7,498,282, which is incorporated herein by reference.

The ethylene-α-olefin block copolymer described herein includes various amounts of "hard" and "soft" segments. "Hard" segments are blocks of polymerized units in which ethylene is present in an amount greater than 95 wt. %, or greater than 98 wt. % based on the weight of the polymer, up to 100 wt. %. In other words, the comonomer content (content of monomers other than ethylene) in the hard segments is less than 5 wt. %, or less than 2 wt. % based on the weight of the polymer, and can be as low as zero. In one or more embodiments, the hard segments include all, or substantially all, units derived from ethylene. "Soft" segments are blocks of polymerized units in which the comonomer content (content of monomers other than ethylene) is greater than 5 wt. %, or greater than 8 wt. %, greater than 10 wt. %, or greater than 15 wt. % based on the weight of the polymer. In one or more embodiments, the comonomer content in the soft segments can be greater than 20 wt. %, greater than 25 wt. %, greater than 30 wt. %, greater than 35 wt. %, greater than 40 wt. %, greater than 45 wt. %, greater than 50 wt. %, or greater than 60 wt. % and can be up to 100 wt. %.

The soft segments can be present in the ethylene-α-olefin block copolymer described herein from 1 wt. % to 99 wt. % of the total weight of the ethylene-α-olefin block copolymer, or from 5 wt. % to 95 wt. %, from 10 wt. % to 90 wt. %, from 15 wt. % to 85 wt. %, from 20 wt. % to 80 wt. %, from 25 wt. % to 75 wt. %, from 30 wt. % to 70 wt. %, from 35 wt. % to 65 wt. %, from 40 wt. % to 60 wt. %, or from 45 wt. % to 55 wt. % of the total weight of the ethylene-α-olefin block copolymer. Conversely, the hard segments can be present in similar ranges. The soft segment weight percentage and the hard segment weight percentage can be calculated based on data obtained from DSC or NMR. Such methods and calculations are disclosed in, for example, U.S. Pat. No. 7,608,668, entitled "Ethylene/α-Olefin Block Interpolymers," filed on Mar. 15, 2006, in the name of Colin L. P. Shan, Lonnie Hazlitt, et. al. and assigned to Dow Global Technologies Inc., the disclosure of which is incorporated by reference herein in its entirety. In particular, hard and soft segment weight percentages and comonomer content may be determined as described in Column 57 to Column 63 of U.S. Pat. No. 7,608,668.

The ethylene-α-olefin block copolymer described herein comprises two or more chemically distinct regions or segments (referred to as "blocks") that can be joined in a linear manner, that is, a polymer comprising chemically differentiated units which are joined end-to-end with respect to polymerized ethylenic functionality, rather than in pendent or grafted fashion.

The ethylene-α-olefin block copolymer described herein can be produced via a chain shuttling process such as described in U.S. Pat. No. 7,858,706, which is herein incorporated by reference. In particular, suitable chain shuttling agents and related information are listed in Col. 16, line 39 through Col. 19, line 44. Suitable catalysts are described in Col. 19, line 45 through Col. 46, line 19 and suitable co-catalysts in Col. 46, line 20 through Col. 51 line 28. The process is described throughout the document, but particularly in Col. 51, line 29 through Col. 54, line 56. The process is also described, for example, in U.S. Pat. Nos. 7,608,668; 7,893,166; and 7,947,793.

In embodiments herein, the ethylene-α-olefin block copolymer has a density of less than 0.900 grams/cubic centimeter (g/cc). All individual values and subranges of a density less than 0.900 g/cc are included and disclosed herein. For example, in one or more embodiments, the ethylene-α-olefin block copolymer has a density of less than 0.895 g/cc, less than 0.890 g/cc, less than 0.885 g/cc, or less than 0.880 g/cc. In other embodiments, the ethylene-α-olefin block copolymer has a density of from 0.850 g/cc to 0.890 g/cc, 0.850 g/cc to 0.880 g/cc, 0.850 g/cc to 0.870 g/cc, 0.860 g/cc to 0.890 g/cc, 0.860 g/cc to 0.880 g/cc, 0.860 g/cc to 0.870 g/cc, 0.870 g/cc to 0.900 g/cc, from 0.875 g/cc to 0.900 g/cc, from 0.870 g/cc to 0.890 g/cc, or from 0.870 g/cc to 0.880 g/cc. Density may be measured according to ASTM D792. In addition to the density, the ethylene-α-olefin block copolymer has a melt index (I2) of at least 10 g/10 min. Individual values and subranges of a melt index (I2) of at least 10 g/10 min are included and disclosed herein. For example, in one or more embodiments, the ethylene-α-olefin block copolymer has a melt index (I2) of at least 15 g/10 min, at least 20 g/10 min, or at least 25 g/10 min. In other embodiments, the ethylene-α-olefin block copolymer has a melt index (I2) from 10 g/10 min to 600 g/10 min, 10 g/10 min to 400 g/10 min, 10 g/10 min to 200 g/10 min, 10 g/10 min to 100 g/10 min, 10 g/10 min to 50 g/10 min, 10 g/10 min to 40 g/10 min, 10 g/10 min to 20 g/10 min, 20 g/10 min to 500 g/10 min, 20 g/10 min to 300 g/10 min, 20 g/10 min to 100 g/10 min, 20 g/10 min to 40 g/10 min, 50 g/10 min to 500 g/10 min, 50 g/10 min to 400 g/10 min, 50 g/10 min to 200 g/10 min, 50 g/10 min to 100 g/10 min, 100 g/10 min to 500 g/10 min, 100 g/10 min to 300 g/10 min, 100 g/10 min to 200 g/10 min, 200 g/10 min to 500 g/10 min, 200 g/10 min to 400 g/10 min, 300 g/10 min to 500 g/10 min, 300 g/10 min to 400 g/10 min, or 400 g/10 min to 500 g/10 min, as measured by ASTM D 1238 (190° C./2.16 kg).

In embodiments herein, the cleansing wipe formed from a nonwoven comprises from 2.5 wt. % to 25 wt. % of the ethylene-α-olefin block copolymer. All individual values and subranges of from 2.5 wt. % to 25 wt. % are included and disclosed herein. For example, in one or more embodiments, the cleansing wipe formed from the nonwoven comprises from 2.5 wt. % to 20 wt. %, 5 wt. % to 20 wt. %, 7.5 wt. % to 20 wt. %, 10 wt. % to 20 wt. %, 10 wt. % to 17.5 wt. %, 10 wt. % to 15 wt. %, or 10 wt. % to 12.5 wt. % of the ethylene-α-olefin block copolymer. In addition to the ethylene-α-olefin block copolymer, the cleansing formed from a nonwoven comprises from 75 wt. % to 97.5 wt. % of the first ethylene/alpha-olefin interpolymer. All individual values and subranges of from 75 wt. % to 97.5 wt. % are included and disclosed herein. For example, in one or more embodiments, in addition to the ethylene-α-olefin block copolymer, the cleansing wipe formed from the nonwoven comprises from 75 wt. % to 95 wt. %, 75 wt. % to 90 wt. %, 75 wt. % to 85 wt. %, 75 wt. % to 80 wt. %, 80 wt. % to 95 wt. %, 80 wt. % to 90 wt. %, 80 wt. % to 85 wt. %, 85 wt. % to 95 wt. %, 85 wt. % to 90 wt. %, or 90 wt. % to 95 wt. % of the first ethylene/alpha-olefin interpolymer.

In embodiments, the cleansing wipe may also comprise additional components, such as, one or more other polymers and/or one or more additives. Such additives include, but are not limited to, antistatic agents, color enhancers, dyes, lubricants, fillers, pigments, primary antioxidants, secondary antioxidants, processing aids, UV stabilizers, anti-blocks, slip agents, tackifiers, fire retardants, anti-microbial agents, odor reducer agents, anti-fungal agents, and combinations thereof.

Cleansing Wipe Layers and Bicomponent Fibers

In one or more embodiments, the first ethylene/alpha-olefin interpolymer and the second ethylene/alpha-olefin interpolymer may be used to form nonwovens (e.g., spunbond nonwovens or meltblown nonwovens) of the cleansing wipe. In one or more embodiments, the cleansing wipe may comprise one or more spunbond nonwovens. In one or more embodiments, the cleansing may comprise one or more meltblown nonwovens.

As used herein, "spunbond" refers to fibers formed by extruding a molten thermoplastic polymer composition as filaments through a plurality of fine, usually circular, die capillaries of a spinneret with the diameter of the extruded filaments then being rapidly reduced and thereafter depositing the filaments onto a collecting surface to form a web or fabric of randomly dispersed spunbond fibers with average diameters generally between about 7 and about 30 microns.

As used herein, "meltblown" refers to fibers formed by extruding a molten thermoplastic polymer composition through a plurality of fine, usually circular, die capillaries as molten threads or filaments into converging high velocity gas streams (e.g. air) which function to attenuate the threads or filaments to reduced diameters. Thereafter, the filaments or threads are carried by the high velocity gas streams and deposited on a collecting surface to form a nonwoven web of randomly dispersed meltblown fibers with average diameters generally smaller than 10 microns.

In one or more embodiments, the cleansing wipe has a $S_aM_bS_c$ configuration, wherein S is a spunbond nonwoven and M is a meltblown layer, "a" and "c" are the number of layers of S and are independent integers ranging from 0 to 5, and "b" is the number of layers of M and is an independent integer ranging from 1 to 5, wherein M comprises the first ethylene/alpha-olefin interpolymer and the second ethylene/alpha-olefin interpolymer described above. For example, the cleansing wipe may have a SMS (where a=1, b=1, and c=1), SMMS (where a=1, b=2, and c=1), SSMSS (where a=2, b=1, and c=2), SMMMS (where a=1, b=3, and c=1), SMMSS (where a=1, b=3, and c=2), SM (where a=1, b=1, and c=0), or other configurations, as "a,", "b," and "c" are independent of each other. All characteristics, values, and subranges of the first ethylene/alpha-olefin interpolymer and the second ethylene/alpha-olefin interpolymer described above are included herein with respect to the meltblown layer (M). For example, in one or more embodiments, the meltblown layer (M) comprises from 75 wt. % to 97.5 wt. % of the first ethylene/alpha-olefin interpolymer. All individual values and subranges of from 75 wt. % to 97.5 wt. % are included and disclosed herein. In one or more embodiments, the meltblown layer (M) comprises from 75 wt. % to 95 wt. %, 75 wt. % to 90 wt. %, 75 wt. % to 85 wt. %, 75 wt. % to 80 wt. %, 80 wt. % to 95 wt. %, 80 wt. % to 90 wt. %, 80 wt. % to 85 wt. %, 85 wt. % to 95 wt. %, 85 wt. % to 90 wt. %, or 90 wt. % to 95 wt. % of the first ethylene/alpha-olefin interpolymer. In addition to the first ethylene/alpha-olefin interpolymer, the meltblown layer (M) comprises from 2.5 wt. % to 25 wt. % of the second ethylene/alpha-olefin interpolymer. All individual values and subranges of from 2.5 wt. % to 25 wt. % are included and disclosed herein. In one or more embodiments, the meltblown layer M comprises from 2.5 wt. % to 20 wt. %, 5 wt. % to 20 wt. %, 7.5 wt. % to 20 wt. %, 10 wt. % to 20 wt. %, 10 wt. % to 17.5 wt. %, 10 wt. % to 15 wt. %, or 10 wt. % to 12.5 wt. % of the second ethylene/alpha-olefin interpolymer.

In one or more embodiments, the cleansing wipe is formed from a nonwoven (e.g., meltblown nonwoven or spunbond nonwoven) comprising bicomponent fibers. In one or more embodiments, the cleansing wipe comprises a bicomponent fiber, wherein the bicomponent fiber has a first region and a second region. The first region is formed from a first composition comprising at least 75 wt. % of polypropylene. All individual values and subranges of at least 75 wt. % of a polypropylene are included and disclosed herein. For example, in one or more embodiments, the first composition comprises at least 80 wt. %, at least 85 wt. %, at least 90 wt. %, at least 92 wt. %, at least 95 wt. %, at least 97 wt. %, at least 99 wt. %, or 100 wt. % of a polypropylene. As used herein, "polypropylene" shall mean polymers comprising greater than 50% by weight of units which have been derived from a propylene monomer. This includes homopolymer polypropylene, random copolymer polypropylene, impact copolymer polypropylene, and propylene-based plastomers and elastomers. These polypropylene materials are generally known in the art.

The first composition may also comprise additional components, such as, one or more other polymers and/or one or more additives. Such additives include, but are not limited to, antistatic agents, color enhancers, dyes, lubricants, fillers, pigments, primary antioxidants, secondary antioxidants, processing aids, UV stabilizers, anti-blocks, slip agents, tackifiers, fire retardants, anti-microbial agents, odor reducer agents, anti-fungal agents, and combinations thereof. In one or more embodiments, the first composition may comprise up to 25 wt. % of propylene-based plastomers or propylene-based elastomers (such as VERSIFY™ polymers available from The Dow Chemical Company and VISTAMAXX™ polymers available from ExxonMobil Chemical Co.), low modulus or/and low molecular weight polypropylene (such as L-MODU™ polymer from Idemitsu), random copolypropylene, or propylene-based olefin block copolymers (such as Intune).

The second region is formed from a second composition comprising the first ethylene/alpha-olefin interpolymer and the second ethylene/alpha-olefin interpolymer described above. All characteristics, values, and subranges of the first ethylene/alpha-olefin interpolymer and the second ethylene/alpha-olefin interpolymer described above are included herein with respect to the second composition. For example, in one or more embodiments, the second composition comprises from 75 wt. % to 97.5 wt. % of the first ethylene/alpha-olefin interpolymer. All individual values and subranges of from 75 wt. % to 97.5 wt. % are included and disclosed herein. In one or more embodiments, the second composition comprises from 75 wt. % to 95 wt. %, 75 wt. % to 90 wt. %, 75 wt. % to 85 wt. %, 75 wt. % to 80 wt. %, 80 wt. % to 95 wt. %, 80 wt. % to 90 wt. %, 80 wt. % to 85 wt. %, 85 wt. % to 95 wt. %, 85 wt. % to 90 wt. %, or 90 wt. % to 95 wt. % of the first ethylene/alpha-olefin interpolymer. In addition to the first ethylene/alpha-olefin interpolymer, the second composition comprises from 2.5 wt. % to 25 wt. % of the second ethylene/alpha-olefin interpolymer. All individual values and subranges of from 2.5 wt. % to 25 wt. % are included and disclosed herein. In one or more embodiments, the second composition comprises from 2.5 wt. % to 20 wt. %, 5 wt. % to 20 wt. %, 7.5 wt. % to 20 wt. %, 10 wt. % to 20 wt. %, 10 wt. % to 17.5 wt. %, 10 wt. % to 15 wt. %, or 10 wt. % to 12.5 wt. % of the second ethylene/alpha-olefin interpolymer.

The second composition may also comprise additional components, such as, one or more other polymers and/or one or more additives. Such additives include, but are not limited to, antistatic agents, color enhancers, dyes, lubricants, fillers, pigments, primary antioxidants, secondary antioxidants, processing aids, UV stabilizers, anti-blocks, slip agents, tackifiers, fire retardants, anti-microbial agents, odor reducer agents, anti-fungal agents, and combinations thereof.

In one or more embodiments, the bicomponent fiber has a sheath/core structure where the sheath comprises the first ethylene/alpha-olefin interpolymer and the second ethylene/alpha-olefin interpolymer described above, and the core comprises at least 75 wt. % of a polypropylene. Of course, other configurations of bicomponent fibers may be used, such as, a side by side arrangement, a pie arrangement, or an islands-in-the sea arrangement.

Test Methods
Density
Density is measured in accordance with ASTM D-792, and expressed in grams/cubic centimeter (g/cc).

Melt Index (I2)
Melt Index is measured in accordance with ASTM D 1238 at 190 Celsius and 2.16 kg, and is expressed in grams eluted/10 minutes (g/10 min).

Brookfield Viscosity
Brookfield Viscosity is measured with a DV-II Pro Extra Viscometer. The instrument uses the Rheocalc V3.3 software which gives a great control and precision of the viscometer. 8 grams of sample is used when using the SC4-31 spindle size. Test temperature is 350 F°. Adequate spindle speed is applied so that the torque is between 40% to 70% level. Viscosity data is recorded after 20 minutes when a stable viscosity reading is obtained, and reported in centipoise (cP).

Conventional GPC
Conventional GPC is obtained by high temperature gel permeation chromatography (GPC) equipment (PolymerChar, Spain). The IR5 detector ("measurement channel") is used as a concentration detector. GPCOne software (PolymerChar, Spain) is used to calculate the z-average (Mz), weight-average (Mw), and number-average (Mn) molecular weight of the polymer and to determine the MWD (=Mw/Mn). The method uses three 10 micron PL gel mixed B columns (Agilent Technologies, column dimension 100×7.6 mm) or four 20 micron PL gel mixed A columns (Agilent Technologies, column dimension 100×7.6 mm) operating at a system temperature of 150° C. Samples are prepared at a 2 mg/mL concentration in 1,2,4-trichlorobenzene solvent containing 200 part per million of antioxidant butylated hydroxytoluene (BHT) for 3 hours at 160° C. with a gentle shaking by autosampler (PolymerChar, Spain). The flow rate is 1.0 mL/min, the injection size is 200 microliters. GPCOne software is used to calculate the plate count. The chromatographic system must have a minimum of 22,000 plates.

The GPC column set is calibrated by running at least 20 narrow molecular weight distribution polystyrene standards. The calibration uses a third order fit for the system with three 10 micron PL gel mixed B columns or a fifth order fit for the system with four 20 micron PL gel mixed A columns. The molecular weight (MW) of the standards range from 580 g/mol to 8,400,000 g/mol, and the standards are contained in 6 "cocktail" mixtures. Each standard mixture has approximately a decade of separation between individual molecular weights. The standard mixtures are purchased from Agilent Technologies. The polystyrene standards are prepared at "0.025 g in 50 mL of solvent" for molecular weights equal to, or greater than, 1,000,000 g/mol, and at "0.05 g in 50 mL of solvent" for molecular weights less than 1,000,000 g/mol. The polystyrene standards are dissolved at 80° C., with gentle agitation, for 30 minutes. The narrow standards mixtures are run first, and in order of decreasing highest molecular weight component, to minimize degradation. The polystyrene standard peak molecular weights are converted to polyethylene molecular weights using Equation (1) (as described in Williams and Ward, J. Polym. Sci., Polym. Letters, 6, 621 (1968)):

$$MW_{PE}=A\times(MW_{PS})^B \quad \text{(Eq. 1)}$$

where MW is the molecular weight of polyethylene (PE) or polystyrene (PS) as marked, and B is equal to 1.0. It is known to those of ordinary skill in the art that A may be in a range of about 0.38 to about 0.44 such that the A value yields 52,000 MWPE for Standard Reference Materials (SRM) 1475a. Use of this polyethylene calibration method to obtain molecular weight values, such as the molecular weight distribution (MWD or Mw/Mn), and related statistics, is defined here as the modified method of Williams and Ward. The number-average molecular weight, the weight-average molecular weight, and the z-average molecular weight are calculated from the following equations.

$$M_{n,cc} = \Sigma w_i / \Sigma(w_i/M_{cc,i}) \quad \text{(Eq. 2)}$$

$$M_{w,cc} = \Sigma w_i M_{cc,i} \quad \text{(Eq. 3)}$$

$$M_{z,cc} = \Sigma(w_i M_{cc,i}^2) / \Sigma(w_i M_{cc,i}) \quad \text{(Eq. 4)}$$

where $M_{n,cc}$, $M_{w,cc}$, and $M_{z,cc}$ (in g/mole) are the number-, weight-, and z-average molecular weight obtained from the conventional calibration, respectively. $w_i$ is the weight fraction of the polyethylene molecules eluted at retention volume $V_i$. $M_{cc,i}$ is the molecular weight (in g/mole) of the polyethylene molecules eluted at retention volume $V_i$ obtained using the conventional calibration (see Equation (1)).

Figure 1:
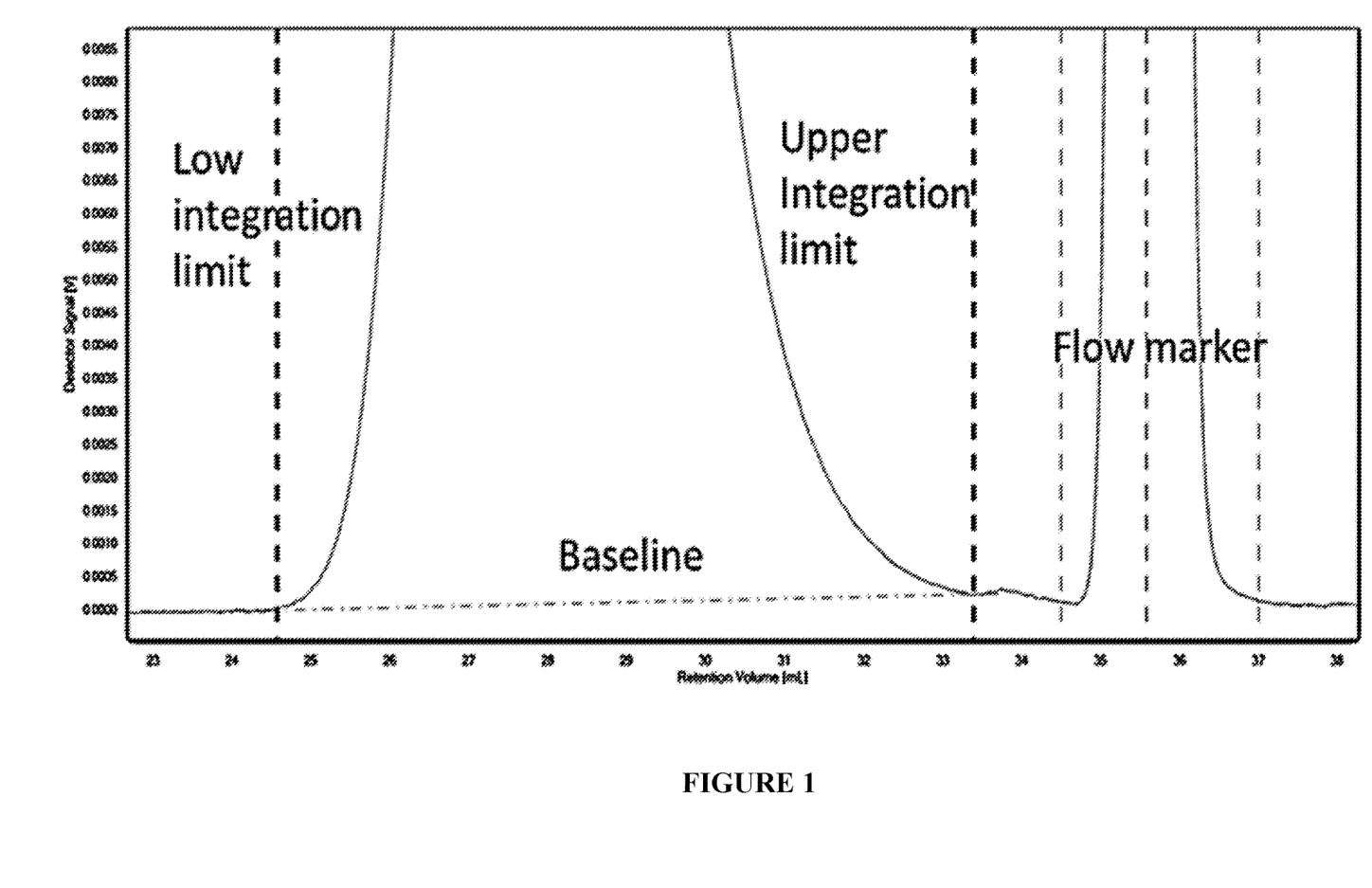
FIG. 1 graphically depicts a chromatogram plot of the detector signal (V) versus retention volume (ml) and the proper baseline and integration limit sets for a sample that exhibits a clear separate antioxidant peak.

The chromatographic peaks should be set to include area marking a significant visible departure from baseline when the chromatogram is viewed at 20 percent peak height. The baseline should not be integrated to less than 100 polyethylene-equivalent molecular weight and care must be used to account for anti-oxidant mismatch from the prepared sample and the chromatographic mobile phase. Referring to FIG. 1, depicted is the proper baseline and integration limit sets for a sample that exhibits a clear separate anti-oxidant peak.

Figure 2:
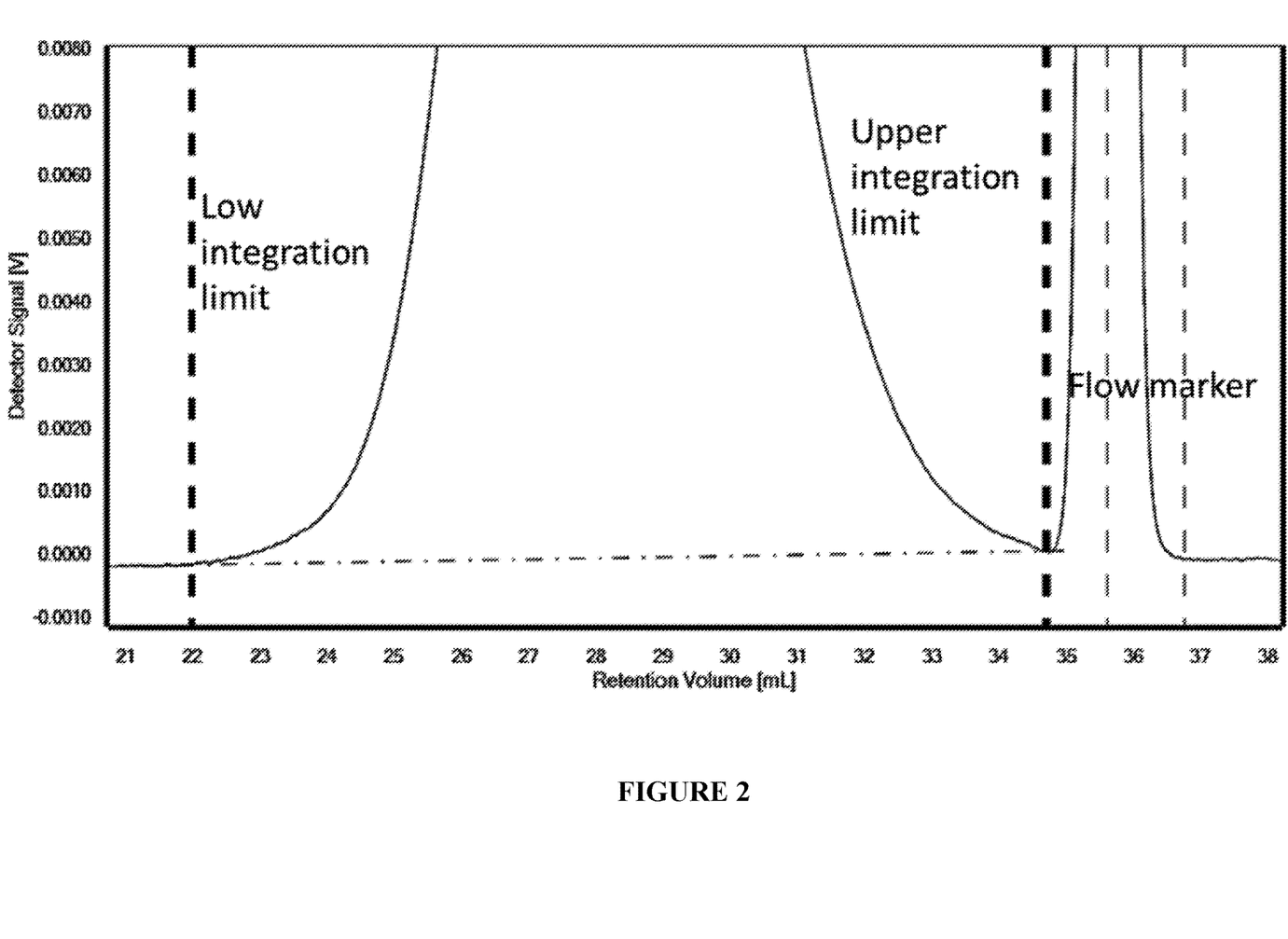
FIG. 2 graphically depicts a chromatogram plot of the detector signal (V) versus retention volume (ml) and the proper baseline and integration limits sets for a sample that shows continuity towards 100 polyethylene-equivalent molecular weight.

Use of a decane flow rate marker is shown in the IR5 chromatogram (see FIGS. 1 and 2). At no point should the baseline (response) Y-value difference between the start and the end of the baseline be greater than 3 percent of the integrated peak height of the chromatogram. In such a case, the chromatographic sample must be handled through proper matching of the sample and mobile phase antioxidant.

Referring to FIG. 2, depicted is the proper baseline and integration limits sets for a sample that shows continuity towards 100 polyethylene-equivalent molecular weight. At no point should the end integration limit be set lower than 100 polyethylene-equivalent molecular weight.

w (wt. fraction greater than $10^5$ g/mole) is calculated according the MWD curve ($w_i$ versus log $M_{cc,i}$) obtained from GPCOne software according to Equation (5)

$$w = \int_{logM_{cc,i}=5}^{logM_{cc,i}=7} w_i d\log M_{cc,i} / \int_{logM_{cc,i}=2}^{logM_{cc,i}=7} w_i d\log M_{cc,i} \quad \text{(Eq. 5)}$$

Differential Scanning Calorimetry (DSC)

DSC is used to measure the melting and crystallization behavior of a polymer over a wide range of temperatures. For example, the TA Instruments Q1000 DSC, equipped with an RCS (refrigerated cooling system) and an autosampler is used to perform this analysis. During testing, a nitrogen purge gas flow of 50 ml/min is used. Each sample is melt pressed into a thin film at about 175° C.; the melted sample is then air-cooled to room temperature (approx. 25° C.). The film sample is formed by pressing a "0.1 to 0.2 gram" sample at 175° C. at 1,500 psi, and 30 seconds, to form a "0.1 to 0.2 mil thick" film. A 3-10 mg, 6 mm diameter specimen is extracted from the cooled polymer, weighed, placed in a light aluminum pan (ca 50 mg), and crimped shut. Analysis is then performed to determine its thermal properties.

The thermal behavior of the sample is determined by ramping the sample temperature up and down to create a heat flow versus temperature profile. First, the sample is rapidly heated to 180° C., and held isothermal for five minutes, in order to remove its thermal history. Next, the sample is cooled to −40° C., at a 10° C./minute cooling rate, and held isothermal at −40° C. for five minutes. The sample is then heated to 150° C. (this is the "second heat" ramp) at a 10° C./minute heating rate. The cooling and second heating curves are recorded. The cool curve is analyzed by setting baseline endpoints from the beginning of crystallization to −20° C. The heat curve is analyzed by setting baseline endpoints from −20° C. to the end of melt. The values determined are highest peak melting temperature (Tm), highest peak crystallization temperature ($T_c$), heat of fusion ($H_f$) (in Joules per gram), and the calculated % crystallinity for polyethylene samples using: % Crystallinity=(($H_f$)/(292 J/g))×100. The heat of fusion ($H_f$) and the highest peak melting temperature are reported from the second heat curve. The highest peak crystallization temperature is determined from the cooling curve.

Comonomer Distribution Breadth Index (CDBI)

The CDBI is defined as the weight percent of the polymer molecules having a co-monomer content within 50 percent of the median total molar co-monomer content (as reported in WO 93/03093, which is incorporated herein by reference). The CDBI of polyolefins can be conveniently calculated from the short chain branching distribution (SCBD) data obtained from the techniques known in the art, such as, for example, temperature rising elution fractionation ("TREF") as described, for example, by Wild, et al., *Journal of Polymer Science, Poly.* Phys. Ed., Vol. 20, 441 (1982); L. D. Cady, "The Role of Comonomer Type and Distribution in LLDPE Product Performance," *SPE Regional Technical Conference*, Quaker Square Hilton, Akron, OH, 107-119 (Oct. 1-2, 1985); or in U.S. Pat. No. 4,798,081 (Hazlitt, et al.) and U.S. Pat. No. 5,008,204 (Stehling), all of which are incorporated herein by reference.

Herein, CDBI is calculated according to the following steps with the SCBD measured by CEF:

(A) Obtain a weight fraction at each temperature (T) (wT(T)) from 20.0° C. to 119.0° C. with a temperature step increase of 0.200° C. from CEF according to the equation $$\int_{20.0}^{119.9} wT(T) dT = 1.00$$

(B) Calculate the median temperature (Tmedian) at cumulative weight fraction of 0.500 (50%) including soluble fraction. The cumulative weight fraction for the entire elution temperature range (generally between 20.0 to 120.0° C.) is normalized as 1.00

(C) Calculate the corresponding median total comonomer content in mole % (Cmedian) at the median temperature (Tmedian) by using comonomer content calibration versus elution temperature (D) Construct a comonomer content calibration curve by using a series of reference materials (ethylene-octene copolymers) with known amount of comonomer content, i.e., eleven reference materials with narrow comonomer distribution (mono-modal comonomer distribution in CEF from 35.0 to 119.0° C.) with weight-average Mw (by conventional GPC) of 35,000 to 115,000 (measured via conventional GPC) at a comonomer content ranging from 0.0 mole % to 7.0 mole % are analyzed with CEF at the same experimental conditions specified in CEF experimental sections. The comonomer content of the reference materials is determined using 13C NMR analysis in accordance with techniques described, for example, in U.S. Pat. No. 5,292, 845 (Kawasaki, et al.) and by J. C. Randall in Rev. Macromol. Chem. Phys., C29, 201-317, which are incorporated herein by reference.

(E) Calculate comonomer content calibration by using the peak temperature ($T_p$) of each reference material and its comonomer content; The calibration is calculated from each reference material as shown in the below Formula, wherein: $R^2$ is the correlation constant;

$$\ln(1 - comonomercontent) = -\frac{207.26}{273.12 + T} + 0.5533$$

$$R^2 = 0.097$$

(F) Calculate CDBI as the total weight percentage with a comonomer content ranging from $0.5*C_{median}$ to $1.5*C_{median}$. If the density of the polymer is above 0.94, CDBI is thus defined as 100% (see WO1993003093 A1, which is incorporated herein by reference).

Moisture Content Test

Cleansing wipes are formed from a nonwoven. Four cleansing wipes, two comparative examples and two inventive examples (as discussed below) are prepared. The moisture content (%) of each of the example cleansing wipes is determined in accordance with the following test method: (1) 1-2 grams of each example cleansing wipe is cut to produce samples for testing; (2) the weight of each sample is recorded as $W_0$; (3) each sample is submerged for 2 hours in a solution consisting of 10 wt. % of glycol, 1 wt. % of polyvinyl alcohol (PVA), 0.05 wt. % of Ethylenediaminetetraacetic acid disodium salt (Disodium EDTA), and 88.95 wt. % deionized water; (4) each sample is removed from the solution and hung for 20 minutes in ambient room temperature conditions; (5) the weight of each sample is recorded after hanging for 20 minutes as Wi; (6) the moisture content (%) for each example cleaning wipe is calculated by the following equation: $[(W_1-W_0)/W_0]*100\%$. The results from the moisture content test are reported in Table 3 below.

In one or more embodiments herein, the moisture content (%) of the cleansing wipe after hanging for 20 minutes is greater than 800%, as determined by the above test method. All individual values and subranges of greater than 800% are included and disclosed herein. For example, in one or more embodiments, the moisture content (%) of the cleansing wipe after hanging for 20 minutes is greater than 900%, greater than 925%, greater than 950%, greater than 1,000%, or greater than 1,100%. In other embodiments, the moisture content (%) of the cleansing wipe after hanging for 20 minutes is from 801% to 1,200%, from 801% to 1,150%, 801% to 1,100%, 801% to 1,000%, 801% to 900%, 900% to 1,200%, 900% to 1,100%, 900% to 1,000%, or 1,000% to 1,200%.

EXAMPLES

Materials

Polymer 1 (Poly. 1) is a polypropylene polymer manufactured by Cangzhou Tianyuan Plastics New Material Company, LLC. Poly. 1 has a density of 0.900 g/cc.

Polymer 2 (Poly. 2) is an ethylene alpha-olefin interpolymer. Poly. 2 was prepared according to the process and based on the reaction conditions provided for Inventive Example 5 of the description provided in WO 2018/169738 A1, ¶¶ 75-87, which is incorporated herein by reference. Characteristics of Poly. 2 are indicated in Table 1A and Table 1B below.

TABLE 1A

Characteristics—Density, Viscosity, Tm, Tc, and CBDI of Poly 2.

| | Polymer Density (g/cc) | Brookfield Viscosity (cP) | Tm (° C.) | Tc (° C.) | CDBI (%) |
|---|---|---|---|---|---|
| Poly. 2 | 0.930 | 16,850 | 113.4 | 102.7 | 79.3 |

TABLE 1B

Characteristics - $M_{n,\,cc}$, $M_{w,\,cc}$, $M_{z,\,cc}$, $M_{w,\,cc}/M_{n,\,cc}$, $M_{z,\,cc}/M_{n,\,cc}$ and w of Poly 2.

| | $M_{n,\,cc}$ | $M_{w,\,cc}$ | $M_{z,\,cc}$ | $M_{w,\,cc}/M_{n,\,cc}$ | $M_{z,\,cc}/M_{n,\,cc}$ | w (wt. fraction greater than $10^5$ g/mole) |
|---|---|---|---|---|---|---|
| Poly. 2 | 8,554 | 18,877 | 31,142 | 2.2 | 3.6 | 0.17% |

Polymer 3 (Poly. 3) is an ethylene alpha-olefin interpolymer having a melt index (I2) of 500 g/10 min and a density of 0.874 g/cc and is commercially available from Dow Chemical Company (Midland, MI, USA) as a resin under the tradename AFFINITY™ GA 1950.

Polymer 4 (Poly. 4) is an ethylene/alpha-olefin block copolymer having a melt index (I2) of 30 g/10 min and density of 0.880 g/cc and is commercially available from Dow Chemical Company (Midland, MI, USA) as a resin under the tradename INFUSE™ 9900.

Cleansing Wipe Process Conditions and Examples Preparation

Four cleansing wipes, two comparative examples and two inventive examples, formed from nonwovens are fabricated with a meltblown line in accordance with the process conditions reported in Table 2. The meltblown line is equipped with a spinneret die that has 450 holes. The hole size is 0.3 mm in diameter and the hole density is 45 holes/inch. The hot air flow rate is set at 0.8 m³/min. The basis weight of each sample is 70 gsm.

TABLE 2

Process Conditions for the Manufacture of Examples.

| Example Name | Cleansing Wipe Composition | Extrusion Temp. (° C.) | Hot Air Temp. (° C.) | Die-to-Collector Distance (mm) |
|---|---|---|---|---|
| Comparative 1 | 100% Poly. 1 | 280 | 280 | 167 |
| Comparative 2 | 100% Poly. 2 | 225 | 232 | 167 |
| Inventive 1 | 80% Poly. 2 and 20% Poly. 3 | 219 | 231 | 167 |
| Inventive 2 | 95% Poly. 2 and 5% Poly. 4 | 219 | 225 | 167 |

The moisture content (%) of each of the example cleansing wipes is determined in accordance with the test method described above, and the results from the moisture content test are reported in Table 3.

TABLE 3

Moisture Content Data.

| Example Name | Cleansing Wipe Composition | Moisture content (%) after 20 minutes |
|---|---|---|
| Comparative 1 | 100% Poly. 1 | 684% |
| Comparative 2 | 100% Poly. 2 | 714% |

TABLE 3-continued

Moisture Content Data.

| Example Name | Cleansing Wipe Composition | Moisture content (%) after 20 minutes |
|---|---|---|
| Inventive 1 | 80% Poly. 2 and 20% Poly. 3 | 1111% |
| Inventive 2 | 95% Poly. 2. and 5% Poly. 4 | 928% |

As shown in Table 3, the inventive example 1 and the inventive example 2 have a surprisingly high moisture content (%) after hanging for 20 minutes. The comparative example 1 and comparative example 2 do not perform as well for moisture content (%) when compared to the inventive examples.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, if any, including any cross-referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A cleansing wipe formed from a nonwoven comprising: a first ethylene/alpha-olefin interpolymer having
   (i) a density of from 0.911 to 0.939 g/cc,
   (ii) a Brookfield viscosity from 5,000 cP to 40,000 cP,
   (iii) a crystallization temperature (Tc) from 85° C. to 105° C.,
   (iv) a melting temperature (Tm) wherein the first ethylene/alpha-olefin interpolymer has a temperature differential between the Tm and the Tc of less than 12° C. (ΔTm−Tc<12), and
   (v) a molecular weight distribution ($M_w,cc/M_n,cc$) of 1.8 to 3.5; and
   from 2.5 wt. % to 25 wt. % of a second ethylene/alpha-olefin interpolymer having a density of less than 0.900 g/cc and a melt index (I2) of at least 10 g/10 min.

2. A cleansing wipe having a $S_aM_bS_c$ configuration, wherein S is a spunbond nonwoven and M is a meltblown layer, a and c are the number of layers of S and are independent integers ranging from 0 to 5, and b is the number of layers of M and is an independent integer ranging from 1 to 5; and
   wherein M comprises a first ethylene/alpha-olefin interpolymer having
   (i) a density of from 0.911 to 0.939 g/cc,
   (ii) a Brookfield viscosity from 5,000 cP to 40,000 cP,
   (iii) a crystallization temperature (Tc) from 85° C. to 105° C.,
   (iv) a melting temperature (Tm) wherein the first ethylene/alpha-olefin interpolymer has a temperature differential between the Tm and the Tc of less than 12° C. (ΔTm−Tc<12), and
   (v) a molecular weight distribution ($M_{w,CC}/M_{n,CC}$) of 1.8 to 3.5; and
   from 2.5 wt. % to 25 wt. % of a second ethylene/alpha-olefin interpolymer having a density of less than 0.900 g/cc and a melt index (I2) of at least 10 g/10 min.

3. A cleansing wipe formed from a nonwoven comprising a bicomponent fiber, wherein:
   the bicomponent fiber has a first region and a second region,
   the first region is formed from a first composition comprising at least 75 wt. % of a polypropylene;
   the second region is formed from a second composition comprising a first ethylene/alpha-olefin interpolymer having
   (i) a density of from 0.911 to 0.939 g/cc,
   (ii) a Brookfield viscosity from 5,000 cP to 40,000 cP,
   (iii) a crystallization temperature (Tc) from 85° C. to 105° C.,
   (iv) a melting temperature (Tm) wherein the first ethylene/alpha-olefin interpolymer has a temperature differential between the Tm and the Tc of less than 12° C. (ΔTm−Tc<12), and
   (v) a molecular weight distribution ($M_{w,CC}/M_{n,CC}$) of 1.8 to 3.5; and
   from 2.5 wt. % to 25 wt. % of a second ethylene/alpha-olefin interpolymer having a density of less than 0.900 g/cc and a melt index (I2) of at least 10 g/10.

4. The cleansing wipe of claim 1, wherein the second ethylene/alpha-olefin interpolymer has a density from 0.850 to 0.890 g/cc and a melt index (I2) of from 10 g/10 min to 600 g/10 min.

5. The cleansing wipe of claim 1, wherein the second ethylene/alpha-olefin interpolymer is an ethylene/alpha-olefin block copolymer.

6. The cleansing wipe of claim 1, wherein the first ethylene/alpha-olefin interpolymer has an $M_{z,cc}/M_{n,cc}$ less than 3.5.

7. The cleansing wipe of claim 1, wherein the first ethylene/alpha-olefin interpolymer has a weight fraction (w) of molecular weight greater than $10^5$ g/mole, based on the total weight of the first ethylene/alpha-olefin interpolymer, as determined by conventional gel permeation chromatography, of less than 2.5%, or alternatively, less than 1.0%.

8. The cleansing wipe of claim 1, wherein the first ethylene/alpha-olefin interpolymer has a comonomer distribution breadth index of from 50% to 85%.

9. The cleansing wipe of claim 1, wherein the moisture content (%) of the cleaning wipe after hangin for 20 minutes is greater than 800%.

10. The cleansing wipe of claim 1, wherein the cleansing wipe further comprises one or more spunbond nonwovens.

* * * * *